United States Patent [19]

Granger et al.

[11] Patent Number: 5,382,571
[45] Date of Patent: Jan. 17, 1995

[54] CLATHRATES OF PEROXYACIDS, THEIR PREPARATION AND THEIR USES

[75] Inventors: Michel Granger, Chalons Sur Saone; Michel Dupont, Chagny; Henry Ledon, Versailles, all of France

[73] Assignee: Chemoxal S.A., Paris, France

[21] Appl. No.: 844,568

[22] PCT Filed: Jul. 30, 1991

[86] PCT No.: PCT/FR91/00628

§ 371 Date: Mar. 27, 1992

§ 102(e) Date: Mar. 27, 1992

[87] PCT Pub. No.: WO92/02497

PCT Pub. Date: Feb. 20, 1992

[30] Foreign Application Priority Data

Sep. 30, 1990 [FR] France ................ 90 09677

[51] Int. Cl.[6] .............. C07C 409/24; C08B 37/00; A01N 37/16; C11D 3/39; A61K 31/19; A61K 7/00

[52] U.S. Cl. ...................................... 514/58

[58] Field of Search ............... 514/58, 844, 848, 970; 252/186.1, 186.2, 186.25, 186.26, 186.36; 424/62

[56] References Cited

U.S. PATENT DOCUMENTS

| | | | |
|---|---|---|---|
| 4,153,630 | 5/1979 | Ichikawa et al. | 568/751 |
| 4,267,166 | 5/1981 | Yajima | 426/652 |
| 4,540,721 | 9/1985 | Staller | 524/354 |
| 4,758,579 | 7/1988 | Kohl et al. | 514/338 |
| 4,834,985 | 5/1989 | Elger et al. | 424/488 |
| 5,094,761 | 3/1992 | Trinh et al. | 252/8.8 |
| 5,102,564 | 4/1992 | Gardlik et al. | 252/8.8 |
| 5,147,882 | 9/1992 | Psiorz et al. | 514/325 |
| 5,261,245 | 11/1993 | Tanaka et al. | 62/59 |

FOREIGN PATENT DOCUMENTS

0411951 2/1991 European Pat. Off. .
2596617 10/1987 France .

OTHER PUBLICATIONS

"Stabilization of Hydroperoxides by Means of the Formaion of Inclusion Compounds with β-Cyclodextrin", Matsui et al., Bulletin of the Chemical Society of Japan, vol. 43, No. 6, p. 1910.

Kurozumi et al., "Inclusion Compounds of Non-Steroidal Antiinflammatory and Other Slightly Water Soluble Drugs with α-and β-Cyclodextrins in Powdered Form", Chem. Pharm. Bull., vol. 23 (No. 12) pp. 3062–3068 (1975).

*Primary Examiner*—Ronald W. Griffin
*Attorney, Agent, or Firm*—Curtis, Morris & Safford

[57] ABSTRACT

The invention concerns derivatives of peroxyacids consisting of inclusion compounds or clathrates, in a hollow molecule which is capable of behaving as a receiving structure which respect to a given peroxyacid, their process of preparation and their uses.

(No figure)

24 Claims, No Drawings

CLATHRATES OF PEROXYACIDS, THEIR PREPARATION AND THEIR USES

It is an object of the invention to provide new derivatives of peroxyacids, their process of preparation and their uses.

It is known that peroxyacids are compounds which are difficult to handle. In crystallized state, they are indeed very often unstable. With respect to liquid peroxyacids, the fact that they are explosive, makes their purification difficult, and even impossible.

To solve the problem resulting from their unstability and in order to be able to make these compounds easily available, the inventors have studied the possibility of combining them with other molecules.

These operations have led them to study and develop a new series of compounds.

Therefore the aim of the invention is to provide new derivatives of peroxyacids in a form which is stable for a long period of storage, enabling to provide peroxyacids which are easily available when they have to be used.

The invention also aims at a process for obtaining these derivatives which is easy to carry out, as well as their application, in particular in the field of disinfection, bleaching and organic synthesis.

The new derivatives of peroxyacids of the invention are characterized in that they are inclusion compounds, or clathrates, in a hollow molecule which is capable of behaving as a receiving structure with respect to a given peroxyacid.

The association between the peroxyacids and the host molecule is essentially based on the plurality of Van der Waals bonds between the two compounds. Already when the clathrate is placed in solution or upon heating, the inserted substance is released and is therefore available for use.

The molecules which are used as receiving structure are selected among compounds which, under the conditions used for their preparation, are inert with respect to peroxyacids, provide a hydrophobic cavity of suitable shape and dimensions which is capable of containing at least one molecule of peroxyacid, and holding within its cavity the molecule(s) of peroxyacid.

In a general manner, host molecules of this type comprise for example cavitands as suggested by Peterson in Science News, vol. 132, 90–93, 1987 and Milgrom in New Scientist, 61–64, 1988, or cyclophanes (see chapter 11, p. 629 and following, of Odashima et al in Academic Press, 1983, edited by P.M. Keehn and S. M. Rosenfeld).

According to a preferred embodiment of the invention, the receiving molecule has the structure of a cyclodextrin.

It is known that the cyclodextrins (CD) are cyclic oligoglucosides obtained by enzymatic degradation of starch. They are represented by the formula $(C_6H_{10}O_5)_n$.

Inclusion derivatives in cyclodextrins have already been described (see Cyclodextrins and their Inclusion Complexes of J. Szejtli, Akademiai kiado, Budapest, 1982).

Among these derivatives, the inclusion of organic acids and of certain organic hydroxyperoxides has been considered essentially with a view to improve their heat stability and to decrease their vapor tension.

However, the same techniques which were applied to the microencapsulation of $H_2O_2$ have not permitted to isolate crystallized clathrates.

It was therefore completely unexpected to include according to the invention a peroxyacid in a receiving structure of the cyclodextrin type.

Cyclodextrins especially suitable according to the invention comprise alpha-cyclodextrin (or cyclohexamylose), beta-cyclodextrin (or cycloheptamylose) or gamma-cyclodextrin (or cyclooctamylose).

The cyclodextrins used are possibly substituted when it is intended to give them specific properties. By way of example, substitutions with alkyl, maltosyl or hydroxypropyl groups and those described in the article of J. Szejtli, previously mentioned, will be mentioned.

Bearing in mind the process of preparation used, cyclodextrins are more generally hydrated. This residual water content has an advantageous effect on preservation, by promoting a slow escape of the peroxyacid in the humidity of the air.

The diameter of the cavity is from 5 to 6 Angstroms for alpha-cyclodextrin and its depth is of 7 to 8 Angstroms.

To provide for the inclusion of a molecule of peroxyacid, these general dimensions of a receiving structure appear advantageous.

As peroxyacids which can be used for encapsultation in cyclodextrins, there is mentioned:

mono-peroxyacids of structure $R_1CO_3H$, wherein $R_1$ represents an alkyl, aryl, cycloalkyl groups;

diperoxyacids of structure $HO_3C-R_2-CO_3H$, wherein $R_2$ represents a single bond or an alkylene, arylene, cycloalkylene group.

Preferably, the term alkyl or alkylene in the above meanings correspond to radicals comprising from 1 to 12 carbon atoms; the group aryl is preferably a phenyl and the group arylene, a phenylene.

The substituents $R_1$ and $R_2$ are possibly substituted with functional groups, in particular by one or more carboxylic functions, in the form of ester or amide, or salts, for example alkali, alkali-earth, ammonium or phosphonium salts, and/or by means of one or more alkyl, alkoxy, aryl groups, possibly with one or more cycles, amino, alkylamino, acylamino, acyl, nitrile, nitro, trifluoromethyl, sulfonyl, and/or one or more halogen atoms.

According to one of the embodiments of the invention, the peroxyacids are mixed with the corresponding organic acids in amounts which may vary within a large scale ranging from a few percentages up to about 90% by weight, preferably from 10 to about 40%.

According to another embodiment, the peroxyacids which are solid at room temperature are generally obtained as admixtures which are enriched with peroxyacids and which do not contain much non peroxidized acid. The content of peroxyacid is thus more often at least about 80% by weight.

The peroxyacids in solution, for reasons of safety, generally do not contain more than about 40 to 50% peroxyacid, the latter being mixed with the corresponding organic acid and hydrogen peroxide, respectively at a rate of about 10 to 20% and 20 to 25%, by weight, with possibly a catalyst comprising a strong acid such as $H_2SO_4$ or a resin enabling to rapidly reaching the equilibrium of the mixture to be obtained.

The invention particularly concerns clathrates of peracetic acid and those of perpropionic acid. These compounds are in the form of crystalline, white, odorless powders.

According to an aspect of high interest, their peroxyacid content remains stable when stored at room temperature. Their stability is at least as good as that of an aqueous solution, and more generally substantially higher, as for example with perpropionic acid.

These clathrates are also of interest because they enable a manual handling, without particular care and without noxious odors, of known products having corrosive properties, which are often explosive, and have a pronounced odor.

The clathrate also constitutes a means of storing peroxyacid by preventing any pollution by the vessel containing them.

The invention is applicable to aliphatic peroxyacids, which are solid at room temperature, such as perazelaic, percaprylic, perundecynetic, perlauric, monoperoxysuccinic, monoperoxymaleic, monoperoxyglutaric or diperoxysuccinic acids, which are substituted by an alkyl or alkenyl group, such as for example octyl-2-peroxybutanedioic-1,4, or a diperoxyacid such as diperoxy-dodecane dicarboxylic -1,12 acid.

The invention is also applicable advantageously to the peroxybenzoic acids represented by the formula:

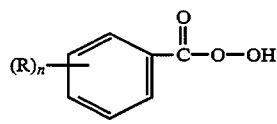

in which:

n is a number from 1 to 5 and R has the meanings given above for $R_1$ and $R_2$.

The acids of this type include peroxybenzoic, metachloroperoxybenzoic, p.tertiobutylperoxybenzoic, p-nitro-peroxybenzoic, monoperphthalic, or aminophthaloyl-peracetic acids,

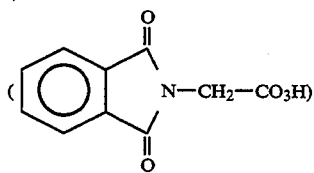

their salts and derivatives, such as the esters or amides as defined above.

The invention also aims at a process for the preparation of inclusion derivatives of peroxyacids.

This process comprises the addition of peroxyacid, in pure form or mixed with a compound capable of behaving as receiving structure for the peroxyacid and the recovery of the clathrate produced.

The reaction is carried out in the absence of solvents or, as a variant, in a heterogeneous solvent medium, or, preferably, in a homogeneous solvent medium.

The peroxyacids which are solid at room temperature are advantageously placed in solution in a suitable solvent, for example water or water mixture or hydrosoluble solvent such as an alcohol, and are added to the receiving compound, which is advantageously also in solution.

The clathrate is precipitated more or less rapidly depending on temperature, speed of addition, relative concentrations. By adjusting these parameters, it is possible to modify the size of the precipitated granules and to define the conditions under which the separation of the precipitate will be facilitated.

After separation, more specially by filtration or centrifugal drying, the precipitate is dried by any adequate means known to one skilled in the art; a particularly efficient and well adapted means consists in drying with a flow of air, such as at a temperature lower than about 50° C.

The water soluble peroxyacids, for example alkylperoxyacids of low molecular weight, for example those having about 1 to 6 carbon atoms, are preferably prepared from the corresponding water soluble organic acids and hydrogen peroxide according to the equilibrium reaction:

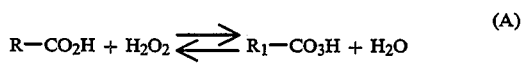

(A)

The inventors have observed that the precursor acid of peroxyacid may give rise to a derivative of inclusion with CD while the hydrogen peroxide cannot be isolated in crystallized form.

To obtain a clathrate which is rich in peroxyacid and relatively poor in precursor acid, there is used with advantage an equilibrium mixture such that reaction (A) is displaced towards the right as much as possible; to reach this state of equilibrium as rapidly as possible, it is advantageous to add a catalyst such as a strong mineral acid in liquid or solid form, such as sulfuric acid or phosphoric acid or a sulfonic resin, for example of the type known under the trade mark DOWEX ®; the limits of concentration of the mixture are easily defined by one skilled in the art depending on the safety and convenience of the operations.

The solutions of peroxyacids or solid mixtures which are rich in peroxyacids may contain the usual stabilizers of peroxidized products, such as for example dipicolinic acid.

The molar ratio peroxyacid/cyclodextrin varies in particular between 0.5 to 3, a satisfactory yield being obtained with a ratio of the order of 1 to 2, more specially near 1. In the case of mixtures of peroxyacid with the corresponding organic acid, the molar ratio peroxyacid+organic acid/cyclodextrin is advantageously of the order of 1 to 2.

In the case of alpha-CD, the precipitation of the clathrate is obtained in a preferred manner by addition for example of the solution of peroxyacid to the saturated aqueous solution of alpha-CD in equimolar quantity (equimolar character on the basis of alpha-CD hydrated with 6H$_2$O); the mixture is thereafter cooled to the vicinity of about 0° C.; the thus precipitated clathrate is filtrated and dried by any known means; particularly interesting results are obtained by drying at a temperature which is relatively low, below than or equal to 35° C., by means of a flow of air passing through the bed of solid granular material.

The advantage of providing peroxyacids as compounds of inclusion facilitates their handling in the various known applications of these products and enables to use them for new applications.

Because of their stability towards temperature and storage, their absence of odor, the total safety in handling, the lowering of their vapor tension and the high content of peroxyacid which is available at the time of use, they present a major interest.

The clathrates of the invention are particularly useful as bleaching agents, in particular for liquid and solid washings.

The germicidal power of the compounds of the invention makes them also valuable as disinfecting agents. They may be used in the known applications of disinfection, such as premises and their atmospheres, materials, ducts and channels, storage containers. For example there may be mentioned the disinfection of breeding premises and animal litters, early vegetable or horticultural greenhouses, silos, toilets, storages and laboratories of the dental trade, public transportation, networks for the distribution of air-conditioned, buildings for collective use, such as sport halls, swimming pools and saunas, networks of drinkable water, ducts for the distribution of fluids, systems of evacuation, furniture, containers for collecting and transporting milk, vegetables and plants, wrappings, vats, concentration material, such as ultrafiltration membranes, for example that used in the food industries, fermenters, buildings and material in pharmaceutical and cosmetic industries, industrial process water, aquiferous or petroliferous forage muds, cutting fluids.

The compounds of the invention are particularly interesting for hospital or medical disinfection, on the one hand for the buildings, and on the other hand, for the medico-surgical material, such as surgical and dental instruments, fibroscopes, hemodialysis apparatuses, syringes and, more generally, the objects which may be subject to an infectious or viral contamination, such as hospital clothing, dressings, sanies.

The compounds of the invention are also suitable as disinfecting agent for use in domestic hygiene, for the disinfection of sinks, restrooms, feeding bottles, contact lenses, tooth brushes.

They may also be used as body hygiene agent, for the asepsis of skin and mucus membranes, for example in the form of soaps or liquid detergents, for example those intended for the asepsis of hands in surgery, as mouth hygiene agent, for example in the form of toothpastes or solutions for mouth washes.

They may also be used as cosmetic agents, for example in order to remove comedons.

Finally, the compounds of the invention may be used as medicine, for example in the form of antiseptic dressing or as an antiseptic agent in order to fight against the infections of the digestive tube, for example intestinal infections, infections of the skin, the mucus membranes and genital organs, in particular the genital cavity.

The compounds of the invention are particularly interesting in view of their germicidal effect, in particular virucidal, algicide, sporicide, bactericidal and fungicidal effect.

They are used, possibly, in association with an inert carrier, in pulverulent form, possibly propelled by means of a gas carrier, in the form of granules, tablets or lozenges and added to the medium in which the peroxyacid is intended to be released.

Tablets of clathrate are for example obtained by dry compression.

By way of example, a clathrate of peracetic acid is prepared by dry compressing 30 mg of clathrate and 70 mg of a carrier containing:

| | |
|---|---|
| AVICEL ® pH 102 | 78.7% |
| starch | 20.0% |
| AEROSIL ® 200 | 0.3% |

-continued

| | |
|---|---|
| magnesium stearate | 1.0% |

In a 100 mg tablet containing a compound according to the invention, it is possible to vary the amount of carrier within large proportions, for example from 50 to 99 mg.

The clathrates may also be arranged in a place to be disinfected, for example an evacuation duct, and they may be allowed to decompose under the action of humidity, the host molecule dissolving and freeing the peroxyacid.

The clathrates of the invention are also particularly interesting in organic synthesis, in all the reactions of oxidation using peroxyacids.

In order to illustrate the invention, examples for the preparation of various clathrates of peroxyacids will be given hereinbelow.

Example 1: Clathrate of Peracetic Acid PAA 1.1 Preparation of the Solution of PAA 10 g of pure acetic acid to which there is possibly added 1.225 g/l dipicolinic acid and 1 g of $H_2SO_4$ 98% are mixed with 14 g of $H_2O_2$ 70%; after 24 hours, a mixture containing 37.5% peracetic acid, 10% acetic acid and 22.5% $H_2O_2$, is obtained.

1.2. Precipitation/Filtration - Drying of Clathrate 1.53 g of this solution (i.e. 7.6 mmoles of PAA and 2.4 mmoles of AA) are added to 80 g of an aqueous solution of alpha-CD containing 9.76 g (10 mmoles) (expressed as an anhydrous product) at 20° C.; after stirring 40 mn at 20° C., the mixture is cooled to 5° C. during 4 h 30; it is wrung on fritted glass and dried with a flow of air at 35° C.: 20 min. at an air speed of 0.17 m/sec and 10 min. at an air speed of 0.06 m/sec; 5.1 g of clathrate are obtained containing 4% PAA and 1,5% acetic acid and about 0.1% $H_2O_2$; the product is stored at room temperature in a glass flask.

The mother liquors containing alpha-CD and possibly PAA may be recycled and added with the above quantities of components.

Example 2: Clathrate of Perpropionic Acid PPROPA 2.1. Preparation of the Peroxyacid To 2.48 g of pure propionic acid containing 1% by weight of sulfuric acid and possibly 0.12% by weight of dipicolinic acid, 2.53 g of $H_2O_2$ 70% are added; after 48 hours, this solution contains 21.9% $H_2O_2$, 34.8% of peracid and 17% of propionic acid.

2.2. Preparation of Clathrate

In a vat containing 24 g of mother liquor from a previous crystallization, 0.74 g of alpha-CD and 5.4 g of water and 500 mg of crystals of clathrate used as primer are added, and, by means of a dosing pump, there are simultaneously added during one hour, 83.9 g of alpha-CD containing 10.5 mmoles of alpha-CD and 2.22 g of the perpropionic acid solution; stirring is allowed to proceed for 1 hour at 22° C.

After filtration and drying in a manner similar to example 1, there is obtained 11.1 g of a dry product containing 3.8% of perpropionic acid and 2.9% of propionic acid and 0.16% of $H_2O_2$.

Storage Stability of the Clathrates of PAA and Perpropionic Acid

After 70 days of storing at room temperature, the clathrate obtained in example 1 has a titer equivalent to 94% of the initial titer.

After 50 days of storage at room temperature, the clathrate of perpropionic acid obtained in example 2 has a titer which is equivalent to 97% of the initial peroxyacid titer.

The mother liquor of perpropionic acid maintained under the same conditions for 11 days has only a titer of 95% of the initial peroxyacid titer.

Example 3: Clathrate of Monoperoxysuccinic Acid PSA

The initial peroxyacid is a solid product having a titer of 81% PSA, 6% acid and 0.9% $H_2O_2$.

4.2 g of an aqueous solution containing 5.12 mmoles of PSA and 0.43 mmole of acid is prepared and it is rapidly added to 136.5 g of a beta-cyclodextrin solution at 46° C. containing 5.5 mmoles of beta-CD.

Cooling is allowed to proceed slowly (6 hours) to 10° C. under stirring.

After filtration and drying, 5.2 g of precipitate containing 2.3% peroxyacid are collected.

Example 4: Metachloroperbenzoic Acid MCPBA

4.1. Preparation of the Clathrate with Alpha-CD

The initial metachloroperbenzoic acid is a solid having a titer of 87% peroxyacid and 12% metachlorobenzoic acid.

50 g of an aqueous solution containing 6.57 mmoles of alpha-CD (i.e. 6.39 g of anhydrous alpha-CD) is prepared. 1.13 g of MCPBA are added, during a few seconds, while stirring at room temperature. Stirring is continued during 16 hours.

After filtration and drying, there are obtained 4.1 g of a precipitate containing 14% of peroxyacid.

4.2. Preparation of the Clathrate with Beta-CD

A solution containing 91 g water, 23 g ethanol and 6.49 g of beta-CD is prepared at 40° C. A second solution is prepared containing 5 g of ethanol and 0.95 g of MCPBA. This second solution is introduced into the first solution during about one minute, while stirring, at 40° C. The mixture is kept under stirring during 17 h at room temperature.

After filtration and drying, 6.5 g of a dry precipitate containing 9.5% of peroxyacid are obtained.

Example 5: Paratertiobutylperbenzoic Acid PTBPBA

This product contains 90% peroxyacid and 10% paratertiobutylbenzoic acid (PTBBA).

5.1. Preparation of the Clathrate with Alpha-CD 142 g of an aqueous solution containing 12.5 mmoles of alpha-CD (12.2 g of anhydrous alpha-CD) and 42 g of ethanol are prepared. A second solution containing 4 g of ethanol and 2.4 g of PTBPBA is prepared. The alcoholic solution of peracid is added to the first solution, while stirring at room temperature. The reaction is allowed to proceed while stirring during 20 minutes.

After filtration and drying, they are obtained 8.6 g of a precipitate containing 7% of peroxyacid.

5.2. Preparation of the Clathrate with Beta-CD

There is prepared a solution at 50° C. containing 75 g of water, 25 g of ethanol and 6.1 g of beta-CD (i.e. 5.2 mmoles of beta-CD).

A second solution is prepared containing 1.6 g of ethanol and 1 g of peroxyacid. This solution is slowly introduced (during 3 min.) into the first solution at 40° C.

The mixture is allowed to cool during 3 h 45 min. A white precipitate is formed. After filtration and drying, there is obtained 5.6 g of a precipitate containing 7.6% of peroxyacid.

Study of the Disinfecting Power of a Clathrate of Peracetic Acid (PAA)

1. Disinfection tests were made according to the procedure defined in norm AFNOR NFT 72150 by utilizing the following products:

A: a clathrate of PAA containing 4% PAA (by weight),

B: by way of comparison, 35% PAA containing 9% hydrogen peroxide in admixture.

tested germ: *Staphylococcus aureus*, CNCM 53154
time of contact: 5 minutes
decrease of germs in log: 6 log
temperature: 20° C.
Results

| CLATHRATE OF PAA INITIAL numbering: 2.55 $10^7$ germs/ml | | | | |
|---|---|---|---|---|
| Product concentration % (mass/volume) | 0.025% | 0.05 | 0.0625 | 0.0750 |
| Concentration in ppm PAA | 10 | 20 | 25 | 30 |
| Germ tested Staphylococcus aureus | + | 0 decrease 7.4 log | 0 | 0 |

With the product B, the minimum bactericidal concentration is 35 ppm PAA according to the same procedure as the tests made by the inventors, i.e. 0.01% of product.

The minimum bactericidal concentration of PAA clathrate is 20 ppm PAA during 5 minutes. It is 35 ppm PAA with product B, under the same operating conditions. Therefore the clathrate has a better germicidal activity than product B whose efficiency is about 2, i.e. less active than the first one.

2) Other disinfection tests were made according to the procedure of norm AFNOR NFT 72150 by utilizing the following products:

A: a clathrate PAA containing 4% PAA by weight;
C: a commercial solution, by way of comparison, containing 2.5% peracetic acid and 18% hydrogen peroxide in admixture;
time of contact: 5 minutes;
minimum decrease of the demanded bacterial titer: $10^5$/ml;
temperature: 20° C. RESULTS: Germ tested: *Staphylococcus aureus* CNCM 53 154

| Product concentrations | Peracetic acid concentrations | Initial numbering | Final numbering | Decrease in log10 |
|---|---|---|---|---|
| A = 0.04% | 16 ppm | 7.7 $10^8$ b/ml | <1 b/ml | 8.89 |

| Product concentrations | Peracetic acid concentrations | Initial numbering | Final numbering | Decrease in log10 |
|---|---|---|---|---|
| C = 0.25% | 62.5 ppm | 7.7 $10^8$ b/ml | 250 b/ml | 6.49 |

Germ tested: *Pseudomonas aeruginosa* IP A 22

| Product concentrations | Peracetic acid concentrations | Initial numbering | Final numbering | Decrease in log10 |
|---|---|---|---|---|
| A = 0.04% | 16 | 1.1 $10^9$ b/ml | 4.7 $10^3$ b/ml | 5.37 |
| C = 0.25% | 62.5 | 1.1 $10^9$ b/ml | 8.5 $10^3$ b/ml | 5.11 |

Germ tested: *Escherichia coli* CNCM 54 127

| Product concentrations | Peracetic acid concentrations | Initial numbering | Final numbering | Decrease in log10 |
|---|---|---|---|---|
| A = 0.04% | 16 | 7.9 $10^8$ b/ml | <1 b/ml | 8.90 |
| C = 0.25% | 62.5 | 7.9 $10^8$ b/ml | 5.5 $10^3$ b/ml | 5.16 |

Germ tested: *Enterococcus faecium* CIP 5855

| Product concentrations | Peracetic acid concentrations | Initial numbering | Final numbering | Decrease in log10 |
|---|---|---|---|---|
| A = 0.04% | 16 | 6.8 $10^8$ b/ml | <1 b/ml | 8.83 |
| C = 0.25% | 62.5 | 6.8 $10^8$ b/ml | 9.8 $10^2$ b/ml | 5.84 |

Germ tested: *Mycobacterium smegmatis* CNCM 7 326

| Product concentrations | Peracetic acid concentrations | Initial numbering | Final numbering | Decrease in log10 |
|---|---|---|---|---|
| A = 0.4% | 160 | 3.7 $10^7$ b/ml | 20 b/ml | 6.27 |
| C = 1% | 250 | 3.7 $10^7$ b/ml | 190 b/ml | 5.29 |

In view of the above results, it may be observed that whatever the germ tested, the decrease of the bacterial titer is always more important, even much more important with product A than with product C, even though product A has PAA concentration lower than that of product C, the latter being on the other hand associated with another germicidal agent, hydrogen peroxide.

We claim:

1. Derivatives of peroxyacids, which comprise inclusion compounds or clathrates of a peroxyacid in a hollow molecule which is capable of behaving as a receiving structure with respect to said peroxyacid, wherein the molecule behaving as receiving structure has the structure of a cyclodextrin, a cavitand or a cyclophane.

2. Derivatives of peroxyacids according to claim 1, wherein the peroxyacid is a
mono-peroxyacid of structure $R_1$—$CO_3H$, wherein
$R_1$ is an alkyl, aryl or cycloalkyl group,
$R_1$ being unsubstituted or substituted by one or more carboxylic functions in the form of an ester or amide, salt, alkaline salt, alkaline-earth salt, ammonium salt or phosphonium salt, and/or by one or more alkyl, alkoxy or aryl group, and/or by one or more alkyl, alkoxy or aryl group having one or more cycle, and/or by amino, alkylamino, acyl-amino, acyl, nitrile, nitro, trifluoromethyl or sulfonyl, and/or by one or more halogen atom.

3. Derivatives of peroxyacids according to claim 2, wherein the alkyl radical comprises from 1 to 12 carbon atoms and the aryl radical is a phenyl radical.

4. Derivatives of peroxyacids according to claim 1, wherein the peroxyacids used to prepare the clathrates are mixed with the corresponding organic acids in amounts which may vary from a few percentages to about 90% moles, and the peroxyacids solid at room temperature are in the form of mixtures in which the amount of peroxyacid is at least about 80% by weight.

5. Process for the preparation of derivatives of peroxyacids according to claim 1, which comprises adding peroxyacid, pure or in admixture, with a compound adapted to behave as a receiving structure for the peroxyacid and recovering the formed clathrate.

6. Process according to claim 5, wherein the peroxyacids which are solid at room temperature are placed in solution in a suitable solvent and are added to the receiving compound which is in solution and wherein the water soluble peroxyacids are in the form of mixtures with the corresponding carboxylic acids and hydrogen peroxide, and wherein a catalyst is added to these mixtures.

7. Process according to claim 6, wherein the solution of peroxyacid includes a stabilizing agent.

8. Bleaching agents, comprising at least one derivative of peroxyacid according to claim 1.

9. Disinfecting agents, comprising at least one derivative of peroxyacid according to claim 1.

10. Cosmetic agents, comprising at least one derivative of peroxyacid according to claim 1.

11. Agents for body hygiene, comprising at least one derivative of peroxyacid according to claim 1.

12. Medicines including as an active agent at least one derivative of peroxyacid according to claim 1.

13. Agents or medicines according to any one of claims 8 to 12 in the form of powder, tablets or granules.

14. Derivatives of peroxyacids according to claim 1, wherein the cyclodextrin is alpha-cyclodextrin, beta-cyclodextrin or gamma-cyclodextrin.

15. Derivatives of peroxyacids according to claim 4, wherein the peroxyacids used to prepare the clathrates are mixed with the corresponding organic acids in amounts from about 10 to 40% moles.

16. Process according to claim 6, wherein the solvent is water, alcohol or a water-hydrosoluble solvent mixture.

17. Process according to claim 6, wherein the water soluble peroxyacids are alkyl peroxyacids containing from 1 to 6 carbon atoms.

18. Process according to claim 6, wherein the catalyst is a strong mineral acid.

19. Process according to claim 18, wherein the strong mineral acid is sulfuric acid, phosphoric acid or a sulfonic acid.

20. Process according to claim 7, wherein the stabilizing agent is dipicolinic acid.

21. Agents or medicines according to any one of claims 8 to 12, further comprising an inert carrier.

22. Derivatives of peroxyacids according to claim 1, wherein the peroxyacid is a diperoxyacid of structure $HO_3C$—$R_2$—$CO_3H$, wherein $R_2$ represents an alkylene, arylene or cycloalkylene group, $R_2$ being unsubstituted or substituted by one or more carboxylic functions in the form of an ester or amide, salt, alkaline salt, alkaline-earth salt, ammonium salt or phosphonium salt, and/or by one or more alkyl, alkoxy or aryl group, and/or by one or more alkyl, alkoxy or aryl group having one or more cycle, and/or by amino, alkylamino, acylamino, acyl, nitrile, nitro, trifluoromethyl or sulfonyl, and/or by one or more halogen atom.

23. Derivatives of peroxyacids according to claim 22, wherein the alkylene radical comprises from 1 to 12 carbon atoms and the arylene radical is a phenylene radical.

24. Derivatives of peroxyacids according to claim 2, wherein the mono-peroxyacid is peracetic acid.

* * * * *